(12) United States Patent
Young et al.

(10) Patent No.: US 12,083,251 B2
(45) Date of Patent: Sep. 10, 2024

(54) USB SCENT DIFFUSER

(71) Applicant: Aeron Lifestyle Technology, Inc., Fairfield, IA (US)

(72) Inventors: Christopher Young, Rushville, IL (US); Monica Herr Hadley, Fairfield, IA (US); Patrick Guerin, Fairfield, IA (US); Michael Brush, Fairfield, IA (US)

(73) Assignee: Aeron Lifestyle Technology, Inc., Fairfield, IA (US)

( * ) Notice: Subject to any disclaimer, the term of this patent is extended or adjusted under 35 U.S.C. 154(b) by 898 days.

(21) Appl. No.: 16/227,927

(22) Filed: Dec. 20, 2018

(65) Prior Publication Data

US 2020/0197556 A1 Jun. 25, 2020

(51) Int. Cl.
*A61L 9/03* (2006.01)

(52) U.S. Cl.
CPC ............. *A61L 9/03* (2013.01); *A61L 2209/11* (2013.01)

(58) Field of Classification Search
CPC ............................... A61L 2209/11; A61L 9/03
USPC .......................................................... 392/391
See application file for complete search history.

(56) References Cited

U.S. PATENT DOCUMENTS

| | | | | |
|---|---|---|---|---|
| 2,091,420 A | * | 8/1937 | Segal | A41F 11/02 24/504 |
| 2,626,452 A | * | 1/1953 | Gridley | B23B 13/00 414/17 |
| 3,872,280 A | * | 3/1975 | Van Dalen | A61L 9/03 422/305 |
| 5,407,642 A | * | 4/1995 | Lord | A61L 9/12 239/57 |
| 6,609,935 B2 | * | 8/2003 | Huang | H01R 13/66 392/390 |
| 6,805,300 B2 | * | 10/2004 | Munroe | A61L 9/03 239/34 |
| 7,097,161 B2 | * | 8/2006 | Liou | A61L 9/03 261/142 |
| 8,090,244 B2 | * | 1/2012 | Belongia | A01M 1/2077 392/386 |

(Continued)

FOREIGN PATENT DOCUMENTS

| | | | |
|---|---|---|---|
| DE | 202016104899 | * | 8/2016 |
| KR | 1020220128373 | * | 9/2022 |
| WO | WO2022036107 | * | 2/2022 |

OTHER PUBLICATIONS

Translation DE 202013101904 (Year: 2022).*

(Continued)

*Primary Examiner* — Nathaniel E Wiehe
*Assistant Examiner* — Frederick F Calvetti
(74) *Attorney, Agent, or Firm* — ZarleyConley PLC

(57) ABSTRACT

A USB scent diffuser having a first housing rotatably connected to a second housing. Disposed within the first housing is a first circuit board attached to a USB connector, an on/off button, and an indicator light. Disposed within the second housing is a second heat producing, circuit board and a fragrance emitting member. The first and second housing are connected so that the second housing is rotated in relation to the first housing so that the fragrance emitting member is selectively positioned above the second heat producing circuit board.

15 Claims, 6 Drawing Sheets

(56) References Cited

U.S. PATENT DOCUMENTS

| | | | | |
|---|---|---|---|---|
| 8,625,977 B2* | 1/2014 | Cheung | A61L 9/037 | 392/394 |
| 9,254,344 B2* | 2/2016 | Hsu | A61L 9/03 | |
| 9,399,080 B2* | 7/2016 | Irvin | B60H 3/0014 | |
| 10,638,743 B1* | 5/2020 | Shapiro | H01M 10/48 | |
| 11,311,049 B2* | 4/2022 | Hawes | A24F 40/42 | |
| 11,475,759 B2* | 10/2022 | Henry, Jr. | G08C 17/02 | |
| 2003/0087554 A1* | 5/2003 | Huang | H01R 13/66 | 439/620.09 |
| 2003/0206834 A1* | 11/2003 | Chiao | G06F 3/011 | 422/124 |
| 2004/0235430 A1* | 11/2004 | Ma | A61L 9/12 | 455/90.1 |
| 2005/0013728 A1* | 1/2005 | Huang | A61L 9/03 | 422/4 |
| 2006/0193610 A1* | 8/2006 | Han | B60H 1/00264 | 392/390 |
| 2006/0258215 A1* | 11/2006 | Lai | A61L 9/03 | 439/607.01 |
| 2009/0008411 A1* | 1/2009 | Schumacher | A01M 1/2033 | 222/175 |
| 2009/0196587 A1* | 8/2009 | Cheung | A61L 9/14 | 392/394 |
| 2010/0176213 A1* | 7/2010 | Belongia | A01M 1/2077 | 239/56 |
| 2010/0276416 A1* | 11/2010 | Wang | F24C 9/00 | 222/71 |
| 2011/0110823 A1* | 5/2011 | Wheatley | B60H 3/0028 | 422/123 |
| 2011/0132995 A1* | 6/2011 | Perman | A61L 9/03 | 239/34 |
| 2014/0179170 A1* | 6/2014 | De Jong | A61B 5/0066 | 439/669 |
| 2015/0208826 A1* | 7/2015 | Yang | F16M 11/041 | 248/316.1 |
| 2016/0325605 A1* | 11/2016 | Irvin | B60H 3/0035 | |
| 2017/0112955 A1* | 4/2017 | Bourne | B60H 3/00 | |
| 2017/0251721 A1* | 9/2017 | Rostami | A61M 11/042 | |
| 2017/0258132 A1* | 9/2017 | Rostami | A24F 40/40 | |
| 2020/0154783 A1* | 5/2020 | Hawes | A24F 40/48 | |
| 2020/0268923 A1* | 8/2020 | Clock | A61L 9/03 | |
| 2021/0219611 A1* | 7/2021 | Rostami | A24F 40/40 | |

OTHER PUBLICATIONS

Translation CN 204293562 (Year: 2022).*
Translation CN 106231933 (Year: 2022).*
Translation CA2867624 (Year: 2022).*
EP2856892 translation (Year: 2022).*
CN103768638 (Year: 2023).*
EP2105118 (Year: 2023).*
WO2019/182217) (Year: 2023).*
European Communication, "Communication of the Partial Search Report by the European Patent Office in Munich, Germany, for European Application No. 19218984.3", mailed Apr. 24, 2020, 10 pages.

* cited by examiner

USB SCENT DIFFUSER

BACKGROUND OF THE INVENTION

The present invention is directed to a USB scent diffuser and more particularly a USB scent diffuser where a fragrance emitting member is selectively positioned above a heat producing circuit board.

Scent diffusing devices are well-known in the art. With the increase in the use of computers and similar devices having USB ports, scent diffusers having a USB connector have become more common. While useful, problems with USB scent diffusers exist. In particular, based on the position and orientation of USB ports, USB diffusers cannot always be connected in a manner that provides optimum and efficient use. This is a result of a fragrance emitting member not being positioned to efficiently receive heat from a resister. As a result, a need exists in the art for a USB scent diffuser that addresses these problems.

An objective of the present invention is to provide a USB scent diffuser that is selectively rotatable to operate more efficiently.

Another objective of the present invention is to provide a USB scent diffuser where a fragrance emitting member is easily accessible.

These and other objectives will be apparent to those having ordinary skill in the art based upon the following written description, drawings and claims.

SUMMARY OF THE INVENTION

A USB diffuser has a first housing rotatably connected to a second housing with a connecting member. Disposed within the first housing is a first circuit board attached and connected to a USB connector. The first circuit board is also connected to an on/off button, an indicator light, and a second, heat producing, circuit board that is disposed within the second housing and covered by a circuit protecting conformal coating.

The second housing has a top section and a bottom section. The top section is connected to the bottom section with a living hinge, or alternatively has a cover that is connected to the top section with a captured hinge.

On the bottom surface of a top wall of the top section, or the cover, is a retaining bracket. A fragrance emitting member is slidably received within the bracket above, and in spaced relation to the second heat producing circuit board.

DETAILED DESCRIPTION OF THE PREFERRED EMBODIMENTS

Figure 1:
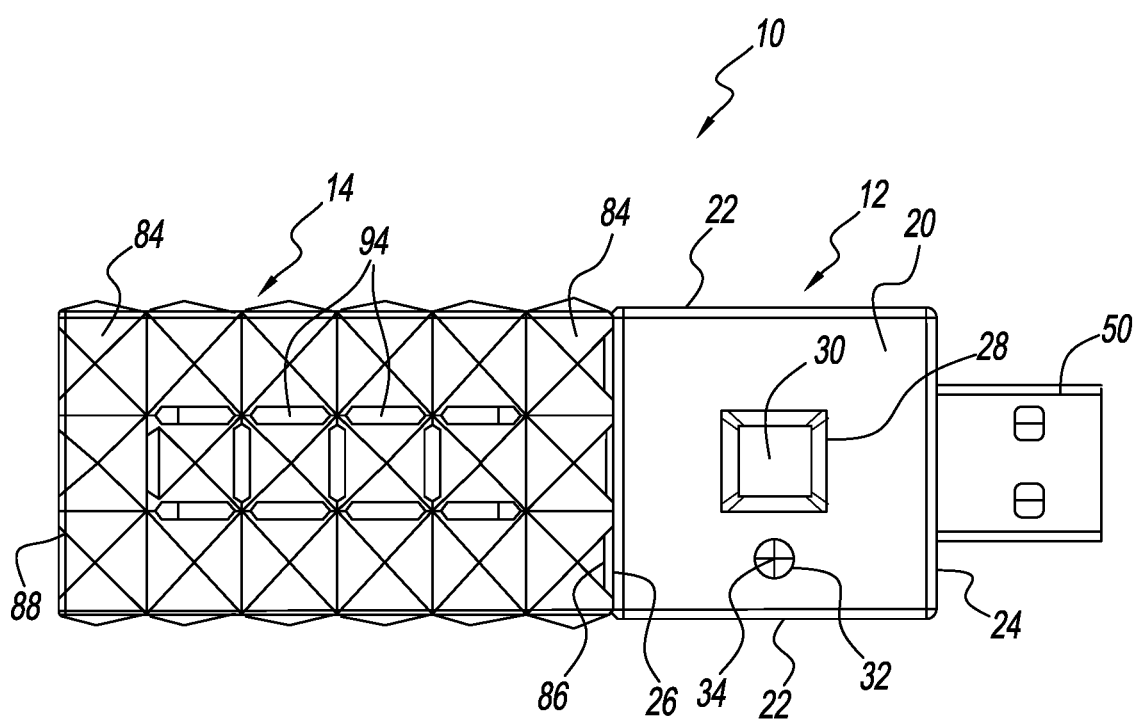
FIG. 1 is a top plan view of a scent diffuser.
Figure 2:
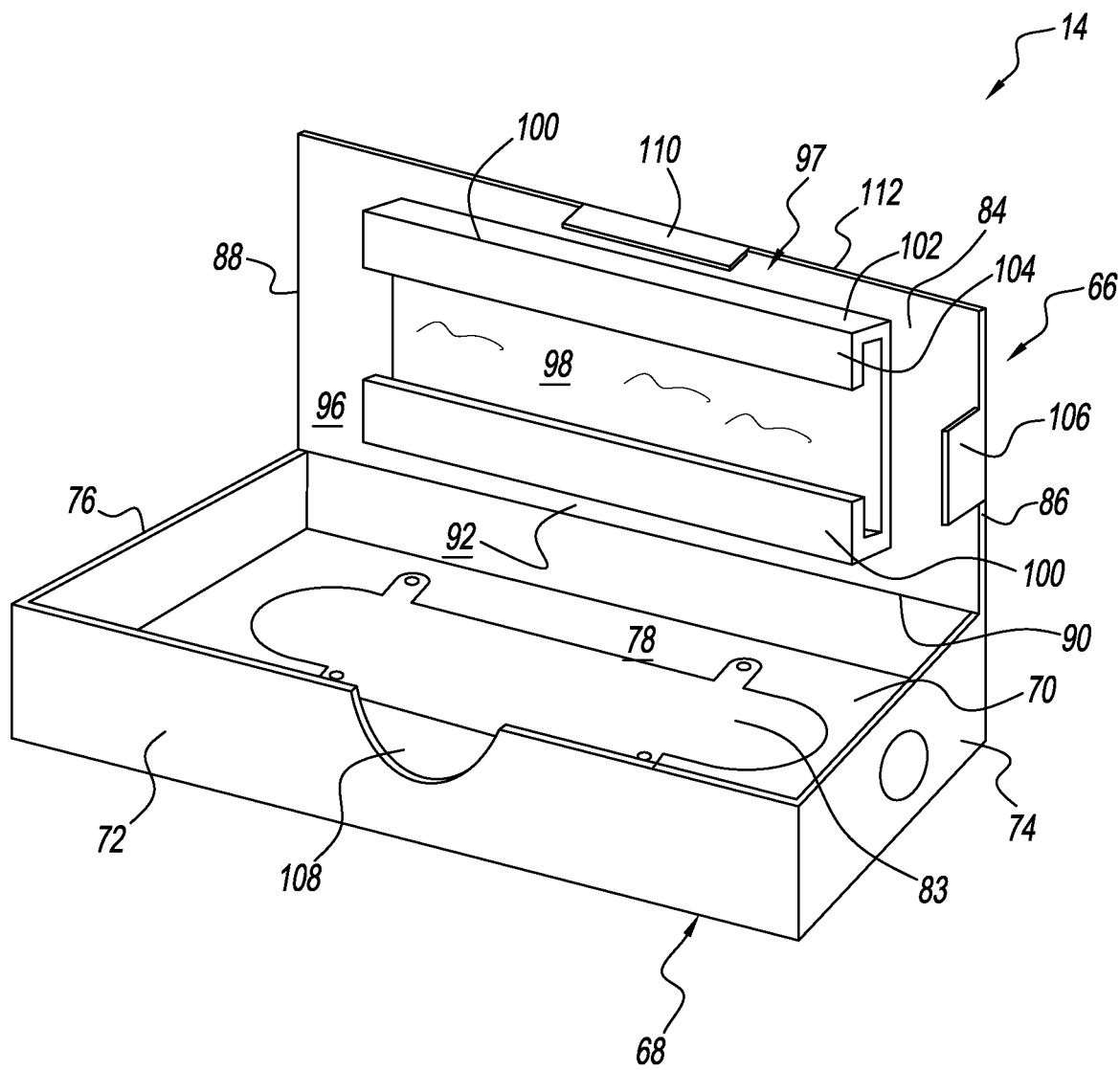
FIG. 2 is a partial perspective view of a scent diffuser.
Figure 3:
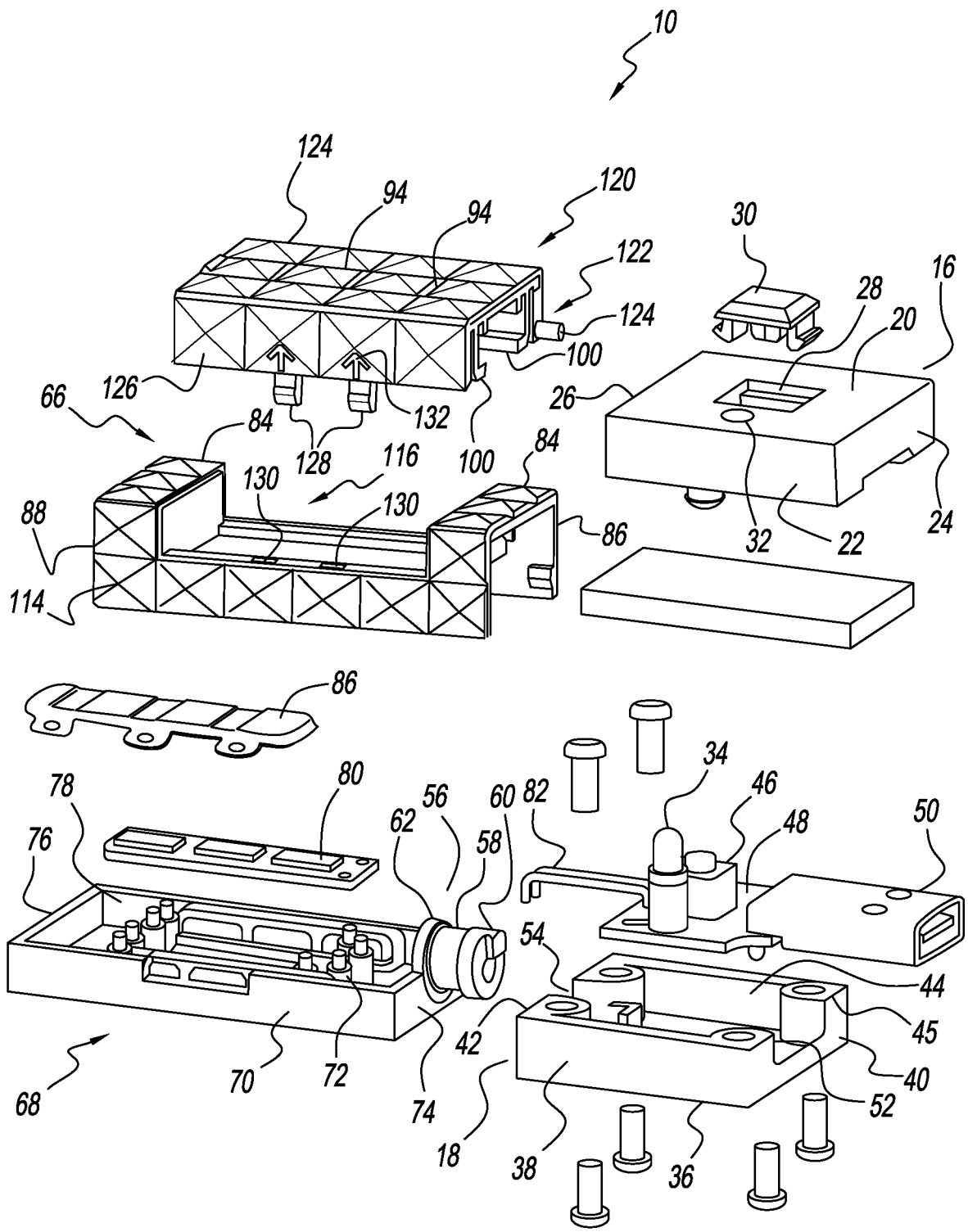
FIG. 3 is an exploded perspective view of a scent diffuser.
Figure 4:
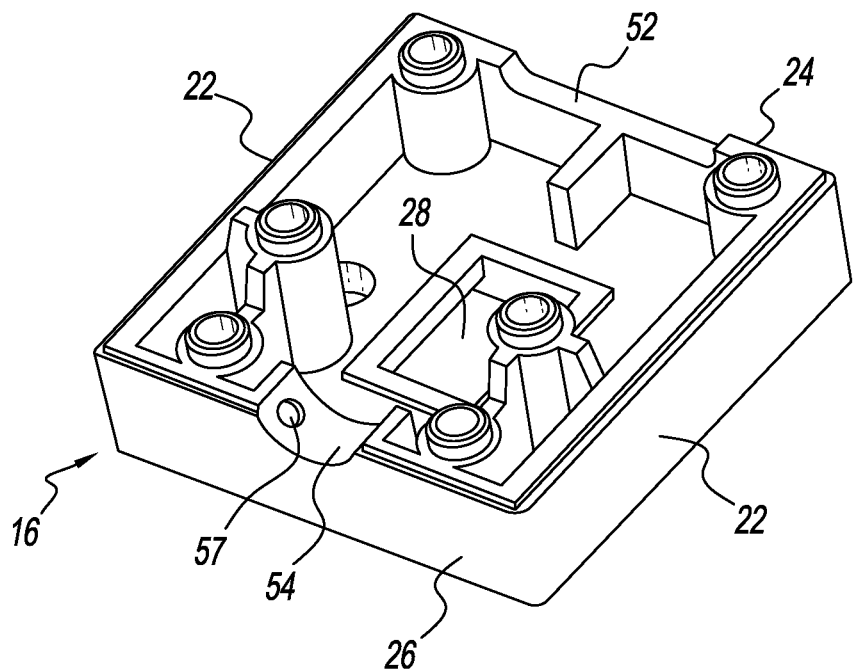
FIG. 4 is a bottom perspective view of a top section of a first housing.
Figure 5:
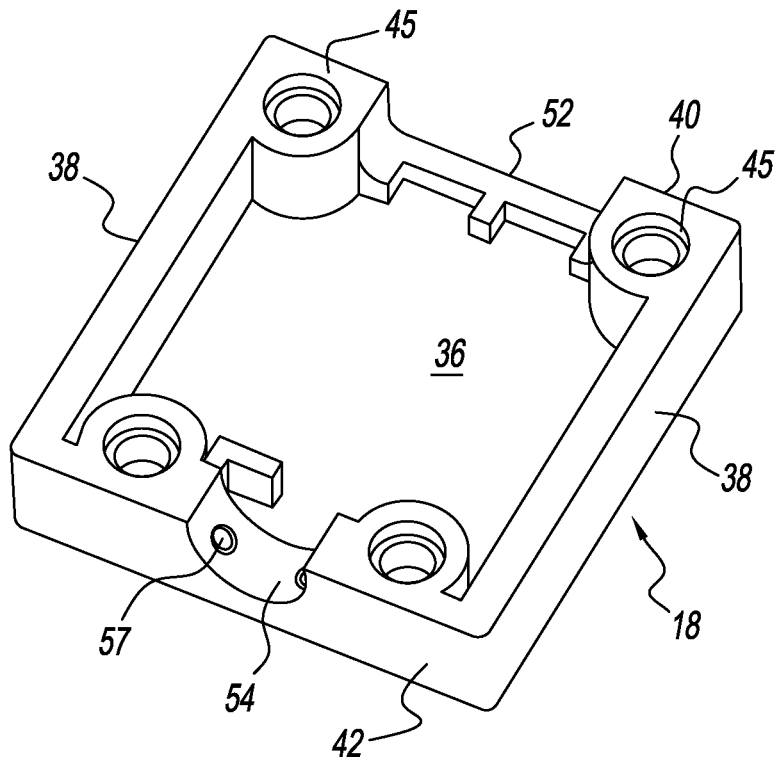
FIG. 5 is a top perspective view of a bottom section of a first housing.
Figure 6:
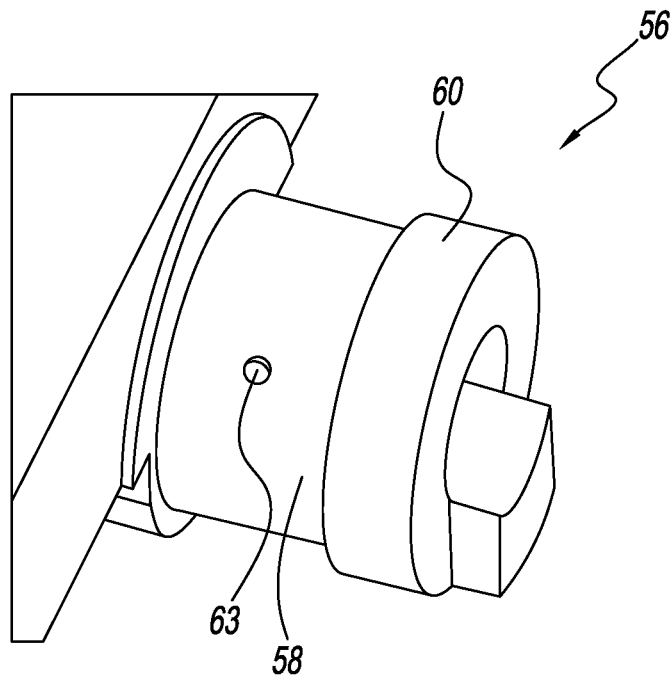
FIG. 6 is an enlarged partial perspective view of a connecting member.
Figure 7:
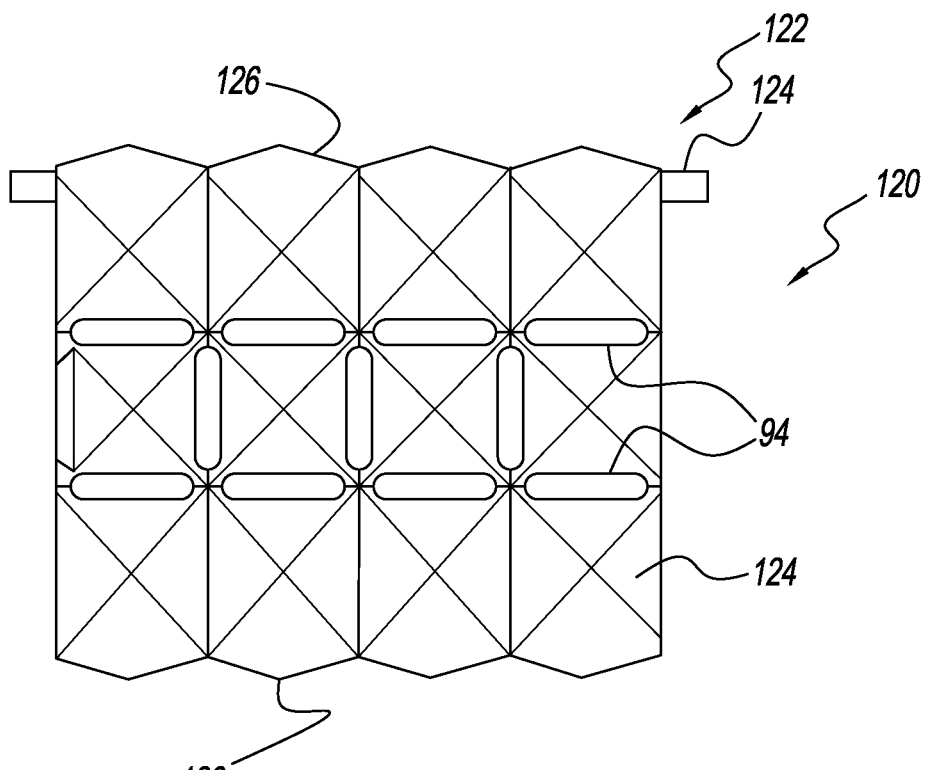
FIG. 7 is a top plan view of a cover with a captive hinge.
Figure 8:
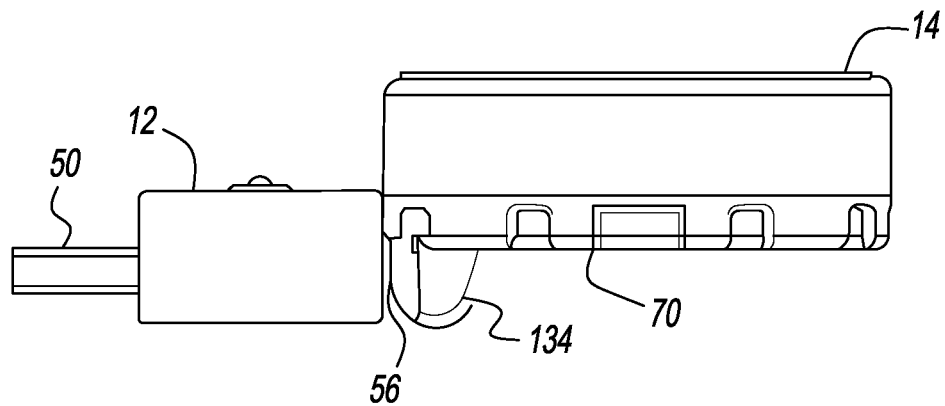
FIG. 8 is a side view of a scent diffuser.
Figure 9:
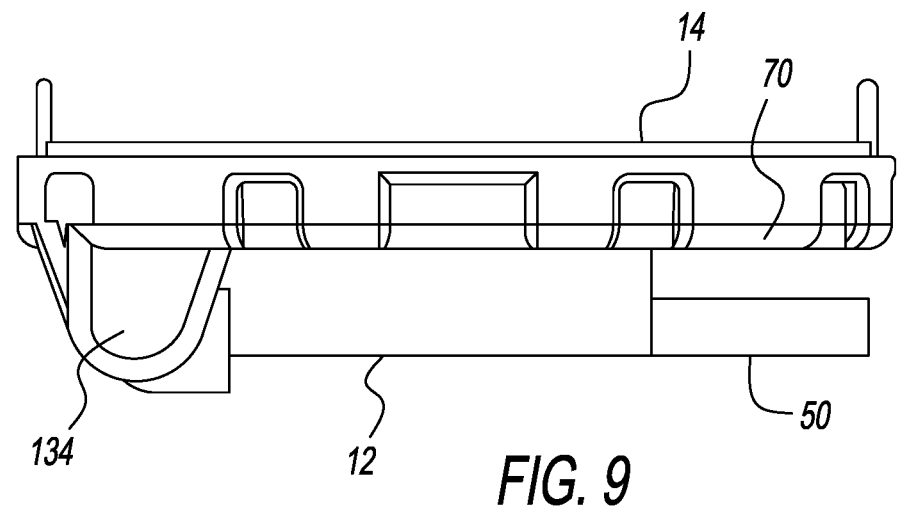
FIG. 9 is a side view of a scent diffuser.
Figure 10:
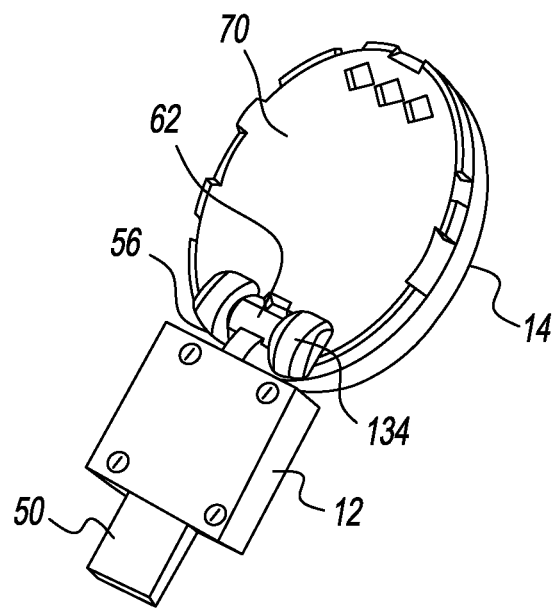
FIG. 10 is a bottom perspective view of a scent diffuser.

Referring to the Figures, a USB scent diffuser 10 includes a first or USB housing 12 that is rotatably connected to a second or fragrance emitting housing 14. The first housing is of any size, shape, and structure and in one example shown is a generally square or rectangular shape. The first housing 12 has a first or top section 16 that is connected to a bottom section 18.

The top section 16 has a top wall 20, side walls 22, a first end wall 24 and a second end wall 26. Preferably, the top wall 20 has a centrally located opening 28 that receives a button cover 30 and a smaller adjacent opening 32 that receives the top of an indicator light 34. The indicator light 34 is of any type and preferably is a duo color LED light. Extending downwardly from the top wall 20 toward the bottom section 18 are a plurality of connecting columns 35 with threaded bores.

The bottom section 18 has a bottom wall 36, side walls 38, a first end wall 40 and a second end wall 42. The top section 16 and the bottom section 18 are connected in any manner to form a hollow chamber 44. In the example shown, the top 16 and bottom 18 sections are connected by four screws inserted in bores 43 that extend through the bottom wall 36 of the bottom section 18 and align with the bores connecting in the columns 35 of the top section 16.

Disposed within the hollow chamber 44 are the indicator light 34, an on/off button 46, and a first circuit board (PCB) 48. The first circuit board 48 is connected to the indicator light 34, the button 36, and a USB connector 50. The USB connector 50 extends through a cut-out opening 52 in the first end walls 24 and 40 of the top 16 and bottom 18 sections. The USB connector 50 is positioned and adapted to be received within a USB port (not shown). The button 36 is positioned to align with opening 28 and button cover 30 and is adapted to turn the diffuser on and off by applying downward manual pressure on the button cover 30.

The second end walls 26 and 42 of the top 16 and bottom 18 sections have a cut-out opening 54 that is adapted to receive a hollow connecting member 56. On the surface of the cut-out opening 54 is a detent hole 57. The connecting member is of any size, shape, and structure. In the example shown, the connecting member 56 has a spool like shape with a smaller diameter in a center cylindrical section 58 and a larger diameter in each end section 60 and 62. A detent 63 is positioned on the central cylindrical section 58 to align with and be selectively received within detent opening 54. Extending away from end section 60 toward and within the first housing 12 is a projection 64. The end section 60 has a diameter larger than cut-out opening 52 and the center section 58 has a diameter smaller than cut-out opening to permit the first housing 12 to rotate about the connecting member 56.

The second fragrance emitting housing 14 has a top section 66 and a bottom section 68. The bottom section 68 has a bottom wall 70, side walls 72, a first end wall 74, and a second end wall 76, that form a lower chamber 78. Disposed within the lower chamber 78 and connected to the bottom wall 70 is a second circuit board 80 that has resistors. The circuit board 80 is connected electrically to the first circuit board 48 by a wire 82 that extends through the hollow connecting member 56. A cover 83 such as a metal plate or a conformal coating is applied to the circuit board 80. The circuit board 80 is connected to the bottom wall 70. The first end 74 of the bottom section 68 has an opening 78 that receives the connecting member 56.

In a first example, the top section 66 of the second housing 14 has a top wall 84, a first end 86, and a second end 88. An edge 90 is hingedly connected to a side wall 72 of the top section 66. The hinge 92 is of any type and preferably a living hinge. The top wall 84 extends the length and width of the bottom section 68 to completely cover the lower chamber 78.

Extending through the top wall 84 are a plurality of fragrance emitting vents 94. Connected to and extending away from a bottom surface 96 of the top wall 84 toward the bottom section 68 is a bracket 97. The bracket 97 is of any size, shape, and structure and is adapted to receive a fragrance emitting member 98. In one example, the bracket 96 has a pair of elongated spaced apart rails 100 that have a vertical section 102 and a horizontal section 104. Adjacent the first end 86 of the top section 66 is a transverse flange 106 that aligns with the space between the rails 100. The fragrance emitting member 98 such as an absorbent pad or the like is slidably received and retained between the rails 100 until the pad 98 engages the transverse flange 106.

The rails 100 are spaced so as to engage an inner surface of the side walls 84 of the bottom section 68. On the side wall 72 opposite the hinge 92 there is a partial cut-out 108 on the outer surface of the side wall 84 that is formed and positioned to receive a thumb press 110 that extends downwardly from the bottom surface 96 of the top section 66 on an edge 112 opposite edge 90.

In an alternative embodiment the top section 66 has side walls 114, partial top wall 84 adjacent the first 86 and second 88 ends, and a cut-out section 116 that extends between the partial top wall 84 and partially down the side walls 114. Hingedly connected to one of the side walls 114 is a cover 120. Preferably, the cover 120 is hingedly connected to the top section with a captured hinge 122 having a shaft 123 that extends beyond a length of the cover 120 and is rotatably received within a bracket (not shown) underneath the top wall 84.

Preferably, the cover 120 has a top wall 124 and a pair of side walls 126 that have a decorative design. The top wall 124 has a plurality of vents 94. The captured hinge 122 is connected to one side wall 126. Extending downwardly from a lower edge 127 of the opposite side wall 126 are a pair of locking prongs 128. The locking prongs 128 are positioned to align with and be selectively received within a pair of locking slots 130 formed in the top of the side wall 114 of the top section 66. On an outer surface of side wall 126 are indicator arrows 132. By applying manual force inwardly and upwardly against the indicator arrows 132, the side wall 126 deforms sufficiently so that hooks 134 on the prongs 128 are released from the slots 130 to permit the cover 120 to open.

In another embodiment, the first and the second housing 12 and 14 are rotatably and pivotally connected. As previously disclosed, the first housing 12 is rotatably attached to a connecting member 56 at the second end wall 26. The connecting member 56 has a first end section 60 that terminates into the center cylindrical section 58. The center section 58 extends from the first end section 60 and terminates in the second end section 62 that is formed as a transverse rod 61. The ends of the transverse rod 62 are pivotally received within a bracket 136 that extends downwardly from the bottom wall 70 of the second housing 14 adjacent the first end 74. The connecting member 56 permits the first housing 12 to pivot underneath and engage the bottom wall 70 of the second housing in a non-operating position.

The second housing 14 preferably is oval in shape with an oval trellis vent 94 design in the top wall 84 of the top section 66. The top section 66 is removably connected to the bottom section 68 by a plurality of connecting prongs 138 that extend from a bottom edge 140 of the side wall 126 of the top section. The connecting prongs 138 are positioned to align with and be selectively received within a plurality of connecting slots 142 formed in the bottom section 68 along an inner surface of the side wall 72.

In operation, a fragrance is placed on the fragrance emitting member 98 and the top section 66 is connected to the bottom section to close the second housing 14. The USB connector 50 is inserted within a USB port (not shown) which supplies electrical power to the diffuser. Based on the connection between the USB connector and the USB port, the second housing 14 is rotated so that the vents 94 are facing upwardly and the fragrance emitting member 98 is positioned above the second circuit board 80 and metal plate 83.

To activate the diffuser 10 the button cover 30 is manually engaged and with downward force button 36 is engaged activating the first circuit board 48. Upon activation, the first circuit board 48 provides power to the indicator light 34 which indicates to a user that the diffuser 10 is activated. The circuit board 48 also provides electrical power via wire 82 to the second circuit board 80. The resistors of the second circuit board 80 produce heat which interacts with the fragrance emitting member 98 causing the applied fragrance to flow through vents 94 providing a pleasant scent to the atmosphere.

The diffuser 10 is turned off by engaging the button cover 30 as previously described. Alternatively, the first circuit board 48 is adapted to shut off at a predetermined time interval such as four hours or the like.

Accordingly, a USB scent diffuser has been disclosed that, at the very least, meets all the stated objectives.

What is claimed is:

1. A scent diffuser, comprising:
   a first housing having a first circuit board disposed within the first housing;
   a USB connector connected to the first circuit board, wherein the USB connector extends through an opening in a first end wall of the first housing;
   a second housing having a fragrance emitting member and a heat producing second circuit board, and a plurality of fragrance emitting vents, wherein the second housing is rotatably connected to the first housing to selectively position the plurality of fragrance emitting vents;
   a hollow connecting member having a center cylindrical section that extends from the second housing through a second end wall of the first housing, opposing the first end wall of the first housing, and into the first housing, wherein the first housing and the second housing are rotatably connected by the hollow connecting member;
   at least one wire connecting the first circuit board to the second circuit board, wherein the at least one wire extends through the hollow connecting member;
   wherein the fragrance emitting member is slidably received from a second end of the second housing towards a first end of the second housing within a bracket attached to a bottom surface of a top wall of the second housing;
   the bracket having a pair of spaced apart rails;
   the pair of spaced apart rails having a vertical section that extends from the top wall to a horizontal section.

2. The diffuser of claim 1 wherein the center cylindrical section of the connecting member extends between a first end section and a second end section of the center cylindrical section.

3. The diffuser of claim 1 wherein the center cylindrical section of the hollow connecting member has a detent that is positioned to align with and selectively be received within a detent hole in an opening on the second end wall of the first housing.

4. The diffuser of claim 1 wherein the first housing has an on/off button, an indicator light, and a button cover positioned to selectively engage the on/off button.

5. The diffuser of claim 1 wherein the first circuit board is adapted to shut the diffuser off after a predetermined amount of time.

6. The diffuser of claim 1 wherein the second housing has a top section having side walls, a partial top wall adjacent the first end and the second end, a cut-out section that extends between the partial top wall and partially down the side walls, and a cover hingedly connected to the top section with a captive hinge.

7. The diffuser of claim 6 further comprising the first housing having a top section connected to a bottom section; the top section having a top wall, side walls, the first end wall, and the second end wall; and the bottom section having a bottom wall, side walls, a first end wall and second end wall.

8. The diffuser of claim 7 wherein the top section and a bottom section of the second housing are connected with a captive hinge, wherein the bottom section has a bottom wall, side walls, a first end wall, and a second end wall.

9. The diffuser of claim 1 further comprising the hollow connection member having a first end section and a second end section, and a projection extending away from the first end section toward and within the first housing.

10. The diffuser of claim 1 further comprising a transverse flange attached to the bottom surface of the top wall of the second housing, wherein the transverse flange is positioned in a space between the pair of spaced apart rails.

11. A scent diffuser, comprising:
   a first housing having a first circuit board disposed within the first housing;
   a USB connector connected to a first circuit board;
   a second housing having a fragrance emitting member and a heat producing second circuit board;
   the second housing is rotatably connected to the first housing by a connecting member having a center cylindrical section; and
   the center cylindrical section of the connecting member has a detent that is positioned to align with and selectively be received within a detent hole in an opening on a second end wall of the first housing.

12. The diffuser of claim 11 further comprising at least one wire connecting the first circuit board to the heat producing second circuit board, wherein the at least one wire extends through the connecting member.

13. The diffuser of claim 11 wherein the connecting member has a spool like shape comprising the center cylindrical section extending between a first end section and a second end section, wherein the center cylindrical section has a diameter smaller than a diameter of the first end section and the second end section.

14. A scent diffuser, comprising:
   a first housing having a first circuit board disposed within the first housing;
   a USB connector connected to a first circuit board, wherein the USB connector extends through an opening in a first end wall of the first housing;
   a second housing having a fragrance emitting member and a heat producing second circuit board, and a plurality of fragrance emitting vents, wherein the second housing is rotatably connected to the first housing to selectively position the plurality of fragrance emitting vents;
   a hollow connecting member having a center cylindrical section that extends from the second housing through a second end wall of the first housing, opposing the first end wall of the first housing, and into the first housing, wherein the first housing and the second housing are rotatably connected by the hollow connecting member;
   at least one wire connecting the first circuit board to the second circuit board, wherein the at least one wire extends through the hollow connecting member;
   wherein the second housing has a top section having side walls, a partial top wall adjacent a first end and a second end, a cut-out section that extends between the partial top wall and partially down the side walls, and a cover hingedly connected to the top section with a captive hinge;
   wherein the second housing has a bottom section having side walls, a bottom wall, a first end wall, and a second end wall that form a lower chamber;
   wherein the top section and the bottom section of the second housing are connected.

15. The diffuser of claim 14 further comprising one of the side walls of the top section of the second housing having a partial cut-out on an outer surface that is formed and positioned to receive a thumb press that extends downwardly from a bottom surface of the top section on an edge.

* * * * *